United States Patent

Nakada et al.

[11] Patent Number: 5,919,993
[45] Date of Patent: Jul. 6, 1999

[54] METHOD FOR PREPARING HALOGENATED BUTENE AND BUTANE

[75] Inventors: Tatsuo Nakada; Hirokazu Aoyama; Satoshi Koyama, all of Osaka, Japan

[73] Assignee: Daikin Industries Ltd., Osaka, Japan

[21] Appl. No.: 08/108,576

[22] PCT Filed: Jan. 12, 1993

[86] PCT No.: PCT/JP93/00027

§ 371 Date: Sep. 3, 1993

§ 102(e) Date: Sep. 3, 1993

[87] PCT Pub. No.: WO93/14051

PCT Pub. Date: Jul. 22, 1993

[30] Foreign Application Priority Data

Jan. 13, 1992 [JP] Japan .................................. 4-003809

[51] Int. Cl.$^6$ ............................. C07C 17/20; C07C 17/08
[52] U.S. Cl. .......................... 570/160; 570/166; 570/168
[58] Field of Search ..................................... 570/160, 166, 570/168

[56] References Cited

U.S. PATENT DOCUMENTS

| 3,965,201 | 6/1976 | Minklei ..................................... 570/160 |
| 4,147,733 | 4/1979 | Fiske et al. ............................. 570/160 |
| 5,146,019 | 9/1992 | Bielefeldt et al. ..................... 570/160 |
| 5,233,105 | 8/1993 | Schwarz et al. . |

FOREIGN PATENT DOCUMENTS

| 1278429 | 9/1968 | Germany . |
| 0425887 | 10/1990 | Germany . |

*Primary Examiner*—Alan Siegel
*Attorney, Agent, or Firm*—Birch, Stewart, Kolasch & Birch, LLP

[57] ABSTRACT

At least one halogenated compound selected from the group consisting of 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, is prepared by reacting 1,1,2,3,4,4-hexachloro-1,3-butadiene with hydrogen fluoride in a gas phase in the presence of a fluorinating catalyst. Desired products can be prepared commercially according to the present invention.

17 Claims, No Drawings

METHOD FOR PREPARING HALOGENATED BUTENE AND BUTANE

This application is a 371 of PCT/JP93/00027 filed Jan. 12, 1993.

BACKGROUND OF THE INVENTION

1. Field of the Invention

The present invention relates to a method for preparing halogenated butene and butane. Particularly, it relates to a method for preparing at least one halogenated compound selected from the group consisting of 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane.

2. Related Art 1,1,1,4,4,4-Hexafluoro-2,3-dichlorobutane, 1,1,1,4,4,4-hexafluoro-2-chloro-2-butene and 1,1,1,2,4,4,4-heptafluoro-2-butene are useful as industrial chemicals and as an intermediate for medicines and agricultural chemicals. In addition, these materials can be a raw material to prepare 1,1,1,2,2,4,4,4-octafluorobutane which can be prepared by adding hydrogen fluoride (HF) to these materials, and which substitutes for HCFC and is used as a foaming agent, a detergent and a heating medium. 1,1,1,4,4,4-Hexafluoro-2,3-dichlorobutane, 1,1,1,4,4,4-hexafluoro-2-chloro-2-butene and 1,1,1,2,4,4,4-heptafluoro-2-butene can be reduced to prepare 1,1,1,4,4,4-hexafluoro-butane which is used as the same applications as those of these materials.

It is known that 1,1,1,2,4,4,4-heptafluorobutene can be prepared by fluorinating hexachlorobutadiene with KF. However, this method is commercially unsuitable, since a reaction procedure is complex, a treatment of KCl produced after the reaction is necessary due to the use of KF, and a cost is high.

It is also known that 1,1,1,4,4,4-hexafluoro-2-chloro-2-butene can be prepared by fluorinating hexachloro-1,3-butadiene with HF in the presence of SbCl$_5$. However, the antimony catalyst is highly corrosive so that this method is not practically useful due to the absence of a material suitable for a reactor. It is not known to commercially prepare 1,1,1,4,4,4-hexafluoro-2,3-dichlorobutane and 1,1,1,2,2,4,4,4-octafluorobutane.

SUMMARY OF THE INVENTION

An object of the present invention is to provide a commercially useful method for preparing 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, which has not been found yet.

The invention intensively studied ways to obtain a commercially useful method for preparing 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, found that these halogenated compounds can be prepared by selecting a suitable catalyst in the gas phase fluorination of easily available 1,1,2,3,4,4-hexachloro-1,3-butadiene, and then completed the present invention.

Namely, the present invention provides a method for preparing at least one halogenated compound selected from the group consisting of 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, which comprises reacting 1,1,2,3,4,4-hexachloro-1,3-butadiene with hydrogen fluoride in a gas phase in the presence of a fluorinating catalyst.

DETAILED EXPLANATION OF THE INVENTION

The raw material 1,1,2,3,4,4-hexachloro-1,3-butadiene can be economically prepared by chlorinating butane.

The catalyst may be a metal fluoride or a metal oxyfluoride. The metal fluoride and the metal oxyfluoride can be prepared, for example, by adding an alkali to a solution of a metal salt to precipitate a metal oxide and then fluorinating the metal oxide with HF. Specific examples of the metal salt are a chloride, a nitrate salt, a sulfate salt and the like. Specific examples of the alkali are ammonia, urea, an alkaline metal hydroxide and the like.

Specific examples of the metal are one metal or a mixture selected from the group consisting of aluminum, chromium, manganese, nickel and cobalt.

The metal fluoride and the metal oxyfluoride can be used with or without supported on a suitable carrier. Specific examples of the suitable carrier are active carbon, aluminum fluoride and the like.

The reaction is usually conducted in a continuous mode. A reaction temperature is usually from 250 to 450° C., preferably from 300 to 400° C. When the reaction temperature is low, it is disadvantageous that the reaction slowly proceeds. A contacting time with the catalyst is usually from 1 second to 10 minutes, preferably from 5 to 50 seconds, more preferably from 10 to 30 seconds. A reaction pressure is not limited, but it is usually from 0.1 to 20 atm, preferably from 1 to 10 atm.

An amount of HF can be selected from a range between 10 and 100 mol per one mol of hexachlorobutadiene, depending on the desired conversion, the ratio of the products, the contacting time and the reaction temperature. The reaction can be conducted in the amount larger than 100 mol of HF, but this is not practical because of low productivity. The reaction product can be fluorinated again by separating a lowly fluorinated material from necessary components and returning the lowly fluorinated material to the reactor, so that a yield of the desired material can be increased.

The reaction converts the raw material to 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and then 1,1,1,2,2,4,4,4-octafluorobutane successively. Accordingly, the conversion is controlled by suitably selecting the reaction temperature, the contacting time and the amount of HF and the lowly fluorinated material is recycled so that the necessary components can be obtained in a good yield.

PREFERRED EMBODIMENTS OF THE INVENTION

The present invention is illustrated by following Examples.

EXAMPLE 1

Pellets of oxides of the metals shown in Table 1 which had a diameter of 3 mm and a height of 3 mm were used.

This catalyst (55 cc) was filled in a reactor tube (diameter: 20 mm) and then fluorinated with HF.

A reaction temperature was adjusted to a temperature shown in Table 1, and then HF (flow rate: 500 cc/min) and 1,1,2,3,4,4-hexachloro-1,3-butadiene (flow rate: 10 cc/min) in gas states were supplied. A product was washed with water and then analyzed by GLC.

The results are shown in Table 1. In the table, R-336 stands for 1,1,1,4,4,4-hexafluoro-2,3-dichlorobutane, R-1326 stands for 1,1,1,4,4,4-hexafluoro-2-chloro-2-butene, R-1327 stands for 1,1,1,2,4,4,4-heptafluoro-2-butene and R-338 stands for 1,1,1,2,2,4,4,4-octafluorobutane.

GLC analysis condition:
3 m of PORAPACK-Q
Temperature: increased from 100° C. at a rate of 10° C./min

TABLE 1

| Metal | Reaction temperature | Products | | | |
|---|---|---|---|---|---|
| | | R-336 | R-1326 | R-1327 | R-338 |
| Cr | 300° C. | 56% | 25% | 14% | 5% |
| Cr | 350° C. | 46% | 34% | 18% | 2% |
| Cr | 400° C. | 43% | 37% | 19% | 1% |
| Al | 400° C. | 25% | 12% | 11% | 2% |
| Mn | 400° C. | 24% | 10% | 8% | 3% |
| Co | 400° C. | 26% | 14% | 10% | 2% |
| Ni | 400° C. | 18% | 9% | 8% | 2% |

What is claimed is:

1. A method for preparing at least one halogenated compound selected from the group consisting of 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, which comprises reacting 1,1,2,3,4,4-hexachloro-1,3-butadiene with hydrogen fluoride in a gas phase in the presence of a fluorinating catalyst.

2. The method according to claim 1, wherein the catalyst is a fluoride and/or oxyfluoride of at least one metal selected from the group consisting of aluminum, chromium, manganese, nickel and cobalt.

3. The method according to claim 1, wherein the catalyst is prepared by fluorinating chromium oxide with hydrogen fluoride.

4. The method according to claim 1, wherein the catalyst is a metal fluoride or metal oxyfluoride prepared by adding an alkali to a solution of a metal salt to precipitate a metal oxide and then fluorinating the metal oxide with hydrogen fluoride.

5. The method according to claim 4, wherein said metal salt is selected from the group consisting of a chloride, a nitrate salt, and a sulfate salt.

6. The method according to claim 4, wherein said alkali is selected from the group consisting of ammonia, urea, and an alkaline metal hydroxide.

7. The method according to claim 4, wherein the metal is selected from the group consisting of aluminum, chromium, manganese, nickel, cobalt, and mixtures thereof.

8. The method according to claim 1, wherein the reaction is conducted at a temperature of from 250° C. to 450° C.

9. The method according to claim 1, wherein the reaction is conducted at a temperature of from 300° C. to 400° C.

10. The method according to claim 1, wherein the contact time of the fluorinating catalyst is from 1 second to 10 minutes.

11. The method according to claim 1, wherein the contact time of the fluorinating catalyst is from 10 to 30 seconds.

12. The method according to claim 1, wherein the reaction is conducted under a pressure of from 0.1 to 20 atmospheres.

13. The method according to claim 1, wherein the reaction is conducted under a pressure of from 1 to 10 atmospheres.

14. The method according to claim 1, wherein the amount of hydrogen fluoride is from 10 to 100 mols per one mol of 1,1,2,3,4,4-hexachloro-1,3-butadiene.

15. A method for preparing at least one halogenated compound from the group consisting of 1,1,1,4,4,4-hexafluoro-2,3-dichlorobutane, 1,1,1,4,4,4-hexafluoro-2-chloro-2-butene, 1,1,1,2,4,4,4-heptafluoro-2-butene and 1,1,1,2,2,4,4,4-octafluorobutane, which comprises reacting 1,1,2,3,4,4-hexachloro-1,3-butadiene with hydrogen fluoride in a gas phase in the presence of a fluorinating catalyst, wherein the catalyst is a fluoride and/or oxyfluoride of at least one metal selected from the group consisting of aluminum, chromium, manganese, nickel and cobalt, and wherein the reaction temperature is from 250° C. to 450° C.

16. The method according to claim 15, wherein the catalyst is prepared by fluorinating chromium oxide with hydrogen fluoride.

17. The method according to claim 15, wherein the reaction temperature is from 300° C. to 400° C.

* * * * *